US00PP23903P3

(12) United States Plant Patent
Pierron-Darbonne

(10) Patent No.: US PP23,903 P3
(45) Date of Patent: Sep. 17, 2013

(54) STRAWBERRY PLANT NAMED 'PLANASA 02-32'

(50) Latin Name: *Fragaria×ananassa*
Varietal Denomination: PLANASA 02-32

(75) Inventor: Alexandre Pierron-Darbonne, Pamplona (ES)

(73) Assignee: Plantas de Navarra, S.A., Valtierra, Navarra (ES)

( * ) Notice: Subject to any disclaimer, the term of this patent is extended or adjusted under 35 U.S.C. 154(b) by 61 days.

(21) Appl. No.: 13/317,795

(22) Filed: Oct. 28, 2011

(65) Prior Publication Data

US 2013/0111639 P1 May 2, 2013

(51) Int. Cl.
*A01H 5/00* (2006.01)

(52) U.S. Cl.
USPC ..... Plt./208

(58) Field of Classification Search
USPC ..... Plt./208
See application file for complete search history.

*Primary Examiner* — Annette Para
(74) *Attorney, Agent, or Firm* — Christie, Parker & Hale, LLP

(57) ABSTRACT

The present invention relates to a new and distinct strawberry variety. The varietal denomination of the new variety is 'PLANASA 02-32'. Among the characteristics which appear to distinguish the new variety from other varieties are a combination of traits which include big size of flower, a big size of calyx relative to corolla and abundant production of red colored, conical shaped, and big fruit size, and medium time of ripening.

11 Drawing Sheets

Botanical classification: *Pragaria×ananassa* 'PLANASA 02-32'.

Varietal denomination: The new plant has the varietal denomination Duch.

BACKGROUND OF THE INVENTION

The new variety of strawberry was created in a breeding program by crossing two parents; in particular, by crossing as seed parent an undistributed strawberry parent designated '94-020' (unpatented) and as pollen parent an undistributed strawberry parent designated '9719' (unpatented). Female and male are selections from breeder's program of Planasa. Both parental varieties are property and have not been commercialized.

The resulting seedling of the new variety was grown and asexually propagated by runners in Segovia, Spain, 3° 59'W., 41° 22'N., 2742 feet elevation. Clones of the new variety were further asexually propagated and extensively tested. This propagation and testing has demonstrated that the combination of traits disclosed herein which characterize the new variety are fixed and retained true to type through successive generations of asexual reproduction.

SUMMARY OF THE INVENTION

The present invention relates to a new and distinct strawberry variety. The varietal denomination of the new variety is 'PLANASA 02-32'. Among the characteristics which appear to distinguish the new variety from other varieties are a combination of traits which include big size of flower, a big size of calyx relative to corolla and abundant production of red colored, conical shaped, and big fruit size, and medium time of ripening (50% of plants with ripe fruits).

COMPARISON NEW VARIETY TO THE PARENTS

The new variety is distinguished therefrom its parents by the following characteristics possessed by 'PLANASA 02-32' which are different than, or not possessed, by the seed parent designated '94-020' (unpatented) and the pollen parent designated '9719' (unpatented).

1. Seed parent '94-020' (unpatented) is less vigorous than the plant of the new variety 'PLANASA 02-32'.
2. In seed parent '94-020' (unpatented) the position of the inflorescence relative to the foliage is above, whereas in the new variety 'PLANASA 02-32' is level with.
3. In seed parent '94-020' (unpatented) and in pollen parent '9719' (unpatented) the fruit size is smaller than in the new variety 'PLANASA 02-32'.
4. In pollen parent '9719' (unpatented) the terminal leaflet is as long as broad, whereas in the new variety 'PLANASA 02-32' is longer than broad.

COMPARISON TO CLOSEST VARIETY

The new variety is closest to the variety 'Sabrosa' (U.S. Plant Pat. No. 16,558) and the variety 'Camarosa' (U.S. Plant Pat. No. 8,708), but is distinguished therefrom by the following characteristics possessed by 'PLANASA 02-32' which are different than, or not possessed by, 'Sabrosa' (U.S. Plant Pat. No. 16,558) or 'Camarosa' (U.S. Plant Pat. No. 8,708).

1. Terminal leaflet in 'Camarosa' (U.S. Plant Pat. No. 8,708) is as long as broad than in 'PLANASA 02-32' one is longer than broad.
2. Size flower in 'Sabrosa' (U.S. Plant Pat. No. 16,558) and 'Camarosa' (U.S. Plant Pat. No. 8,708) is smaller than in 'PLANASA 02-32' one.
3. Length/width ratio of fruit in 'Camarosa' (U.S. Plant Pat. No. 8,708) is as long as broad, whereas length/width ratio in 'PLANASA 02-32' is slightly broader than long.
4. Fruit size in 'Sabrosa' (U.S. Plant Pat. No. 16,558) is smaller than in 'PLANASA 02-32' one.

5. Predominant fruit shape in 'Camarosa' (U.S. Plant Pat. No. 8,708) is wedged, than in 'PLANASA 02-32' the predominant fruit shape is conical.
6. 'Camarosa' (U.S. Plant Pat. No. 8,708) shows a dark red fruit color (RHS red group near 47 B to 47A), whereas in 'PLANASA 02-32' it is a red fruit color (RHS red group near 44 B to 44 A).
7. Insertion of achenes in fruits of 'Sabrosa' (U.S. Plant Pat. No. 16,558) and 'Camarosa' (U.S. Plant Pat. No. 8,708) is level with surface, whereas in the fruits of 'PLANASA 02-32' the insertion of achenes is below surface.
8. Color of flesh in fruits of 'Camarosa' (U.S. Plant Pat. No. 8,708) (RHS red group near 42 A) and in fruits of 'Sabrosa' (U.S. Plant Pat. No. 16,558) (RHS read group near 43 B) is darker than color of flesh in fruits of 'PLANASA 02-32' (RHS orange-red group near 33 B to 33 A).

The difference in the length/width ratio in the terminal leaflet of 'PLANASA 02-32' (designated 02.13.214) and 'Camarosa' (U.S. Plant Pat. No. 8,708) is shown in FIG. 7. The differences in the shape, fruit color and fruit color of flesh in the fruits of 'Camarosa' (U.S. Plant Pat. No. 8,708) and 'PLANASA 02-32' (designated 02.13.214) are shown in FIG. 9 and FIG. 10. The difference in the fruits color of flesh in the fruits of 'PLANASA 02-32' (designated 02.13.214) and 'Sabrosa' (U.S. Plant Pat. No. 16,558) are shown in FIG. 10 and FIG. 11. These differences are maintained during the harvest season.

BRIEF DESCRIPTION OF ILLUSTRATIONS

The accompanying photographs show typical specimens of the new variety, designated 02.13.214 in the illustrations, including fruit, foliage and flower, in color as nearly true as it is reasonably possible to make in color illustrations of this character.

The plants depicted in the drawings were planted Oct. 10, 2010 in the farm of La Mogalla in Cartaya (Huelva), Spain, about 7° W, 37° N, 45 feet elevation.

Drawings were taken Mars-April, 2011 (about Mars 21 and Apr. 6, 2011): minimum temperate about 10 to 12° Centigrade, maximum temperate about 22 to 24° Centigrade.

FIG. 1 shows several plants of the new variety (designated 02.13.214) which exhibit a plant medium dense and the position of the inflorescence relative to foliage is level with.

Figure 1:
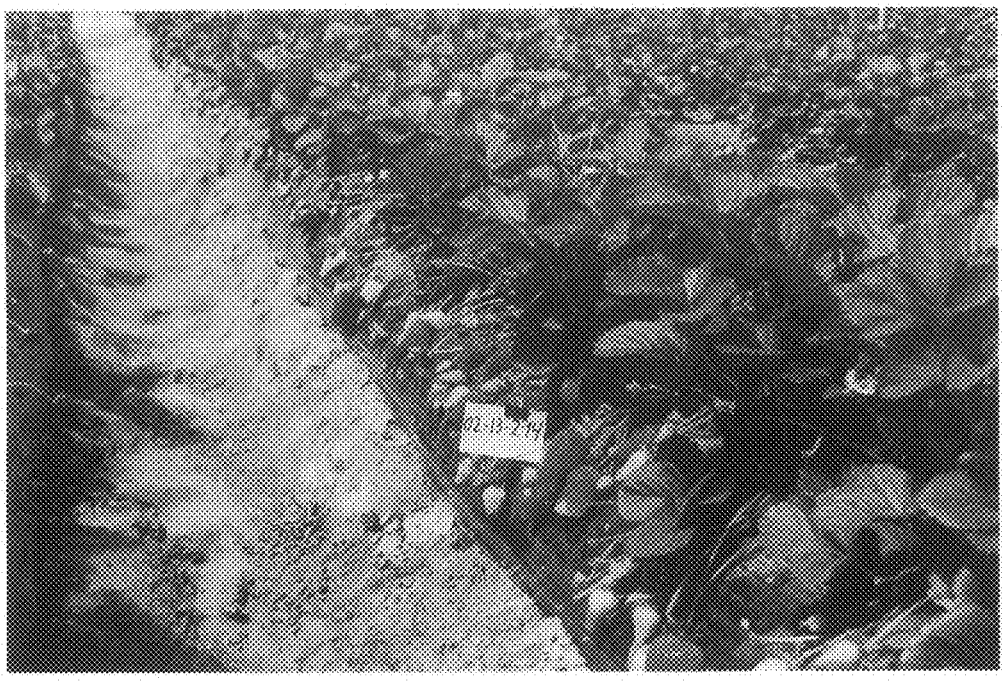
Figure 2:
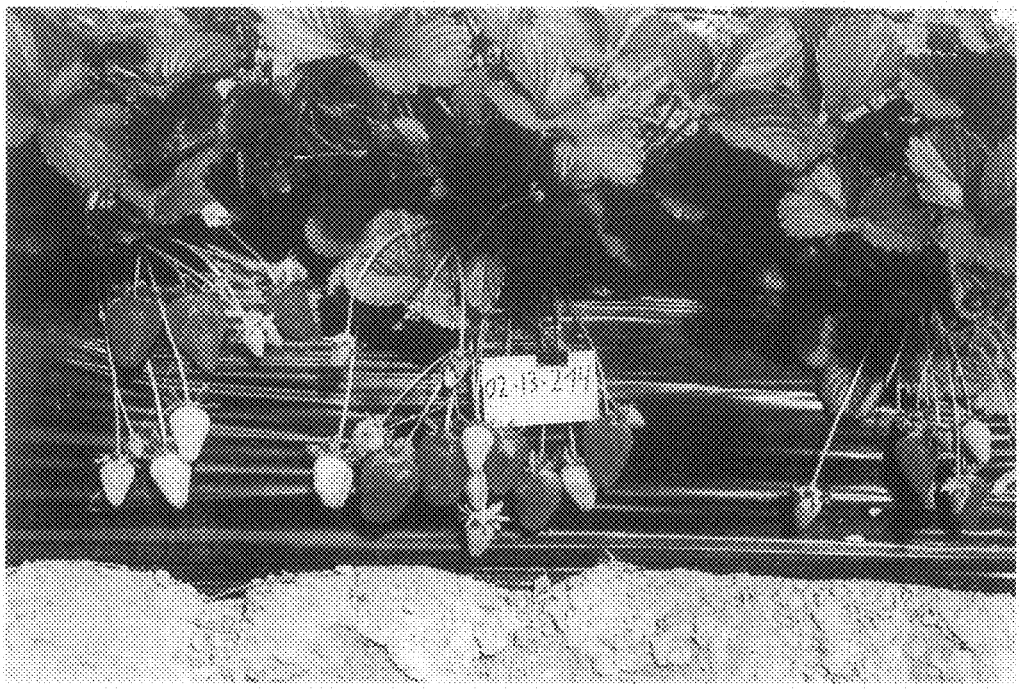
FIG. 2 shows several plants of the new variety (designated 02.13.214) with several red colored and conical shape fruits.
Figure 3:
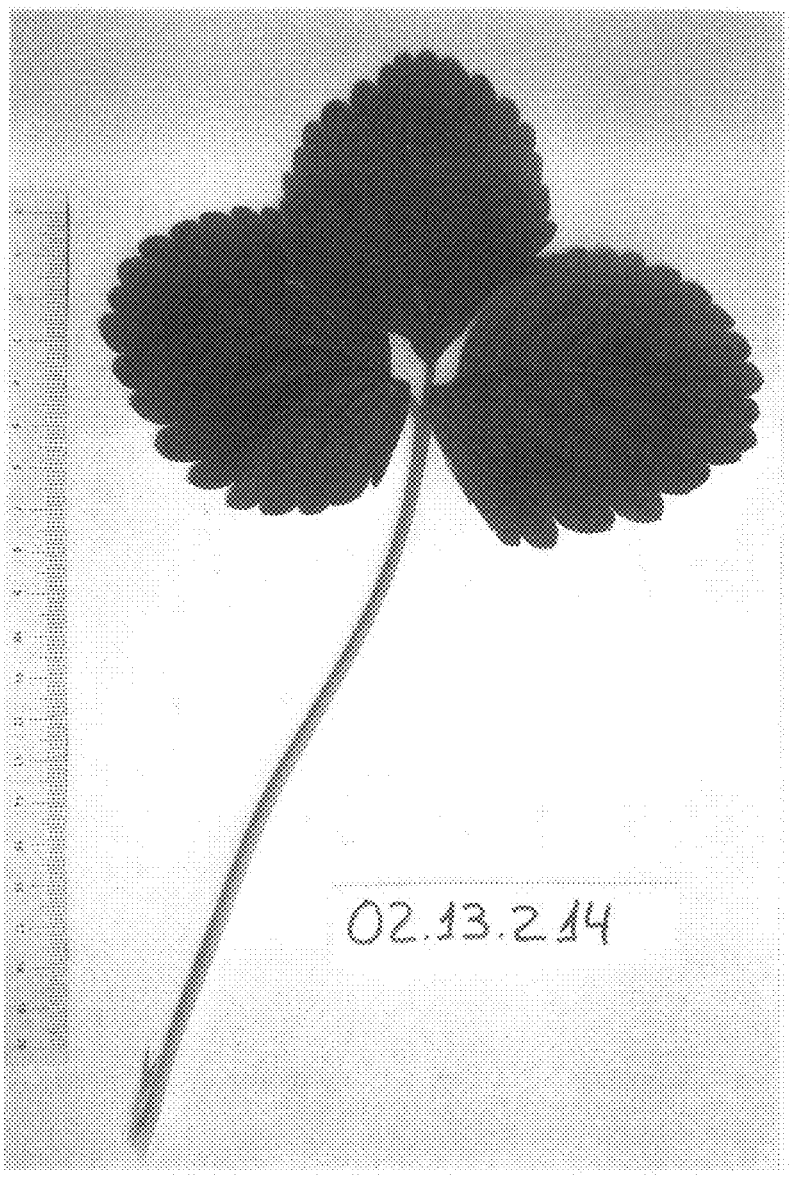
Figure 4:
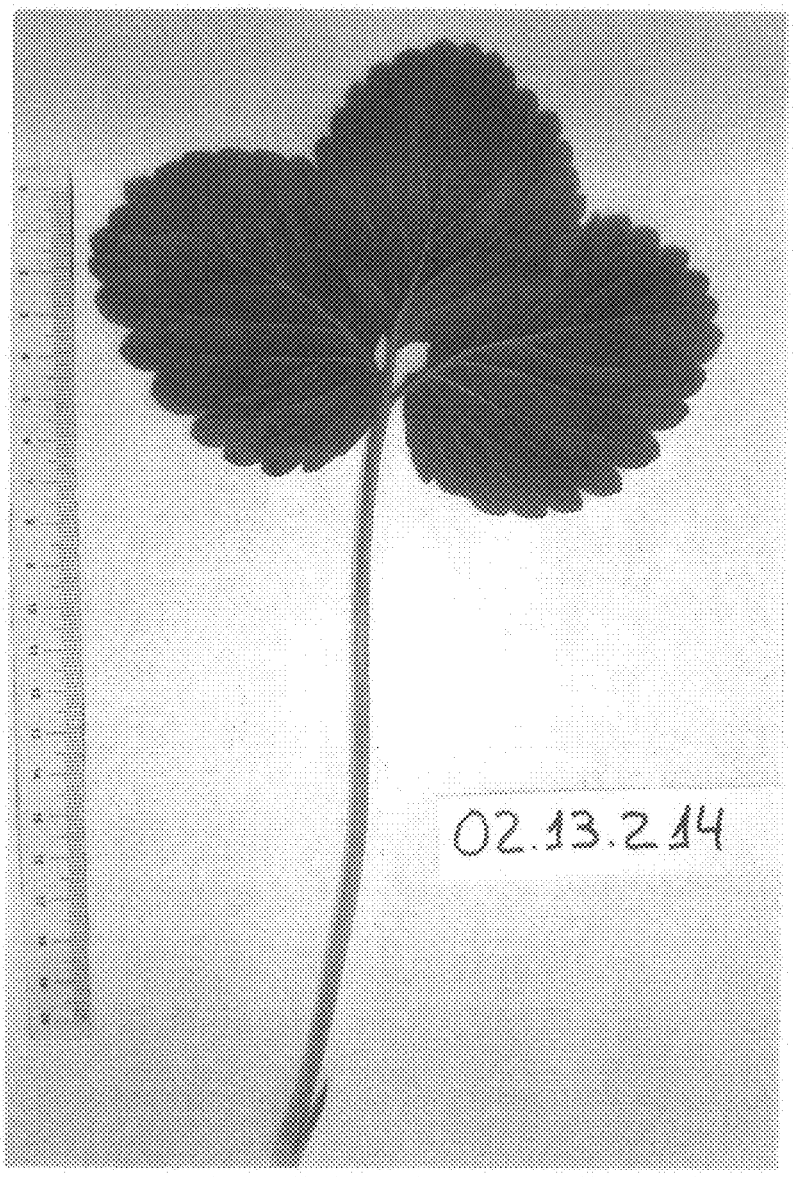

FIG. 3 and FIG. 4 show the upperside and the underside, respectively, of a complete leave of the new variety (designated 02.13.214). In its we can see that the leaf color of upperside of the new variety (designated 02.13.214) is RHS green group color (near 135 B to 136 B) and the leaf color of underside of the new variety (designated 02.13.214) is RHS green group color (near 137 C to 137 B).

Figure 5:
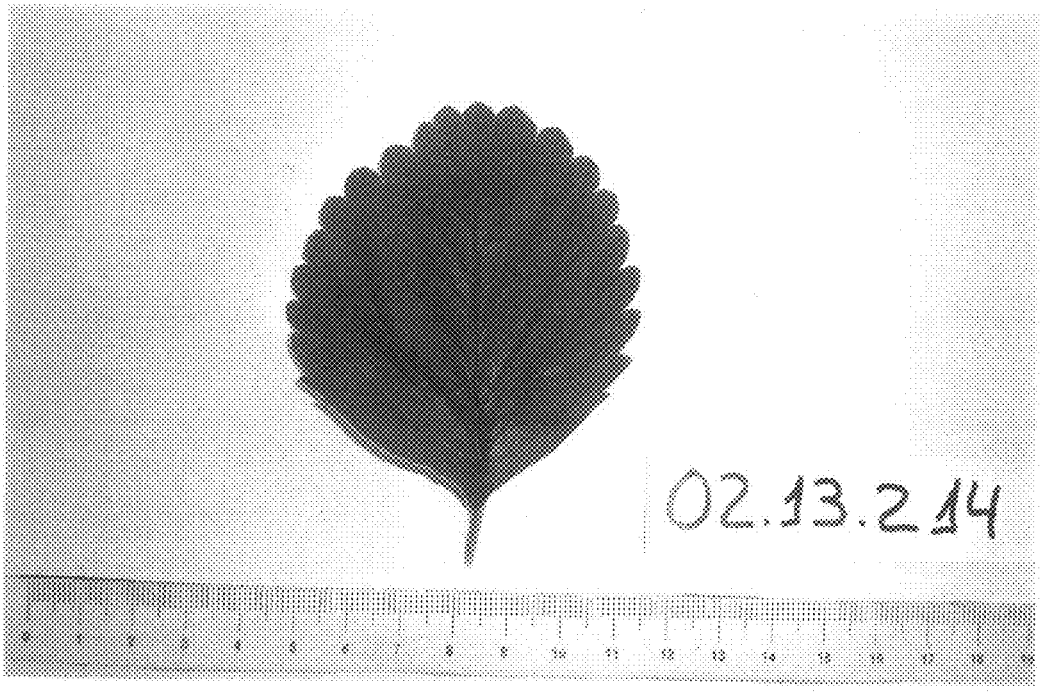
Figure 6:
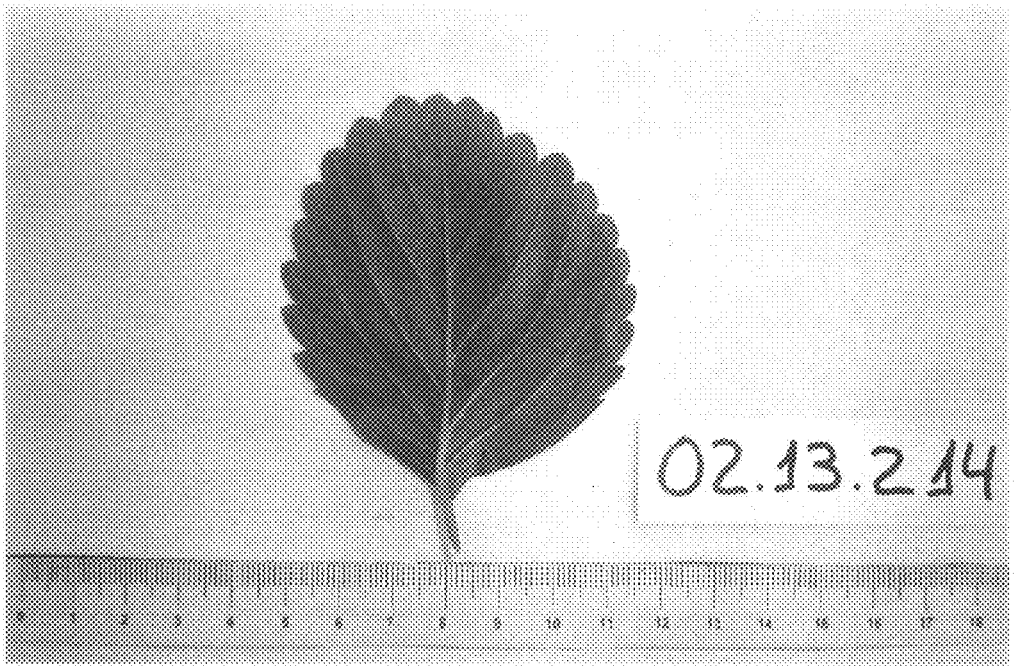

FIG. 5 and FIG. 6 show the upperside and the underside, respectively, of terminal leaflet of the new variety (designated 02.13.214). In its we can see that the leaf color of upperside of the new variety (designated 02.13.214) is RHS green group color (near 135 B to 136 B) and the leaf color of underside of the new variety (designated 02.13.214) is RHS green group color (near 137 C to 137 B).

Figure 7:
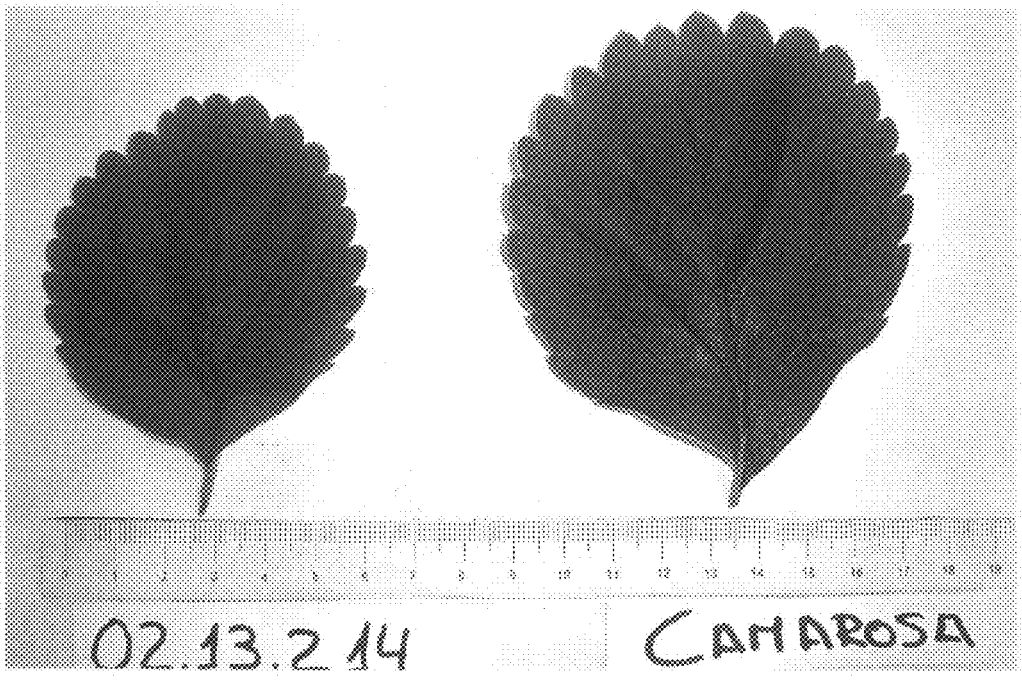

FIG. 7 shows the terminal leaflet of strawberry variety 'Camarosa' (U.S. Plant Pat. No. 8,708) in comparison with the terminal leaflet of the new variety (designated 02.13.214). We can appreciate that the terminal leaflet in strawberry variety 'Camarosa' (U.S. Plant Pat. No. 8,708) is as long as broad than in the new variety (designated 02.13.214) the terminal leaflet is longer than broad.

Figure 8:
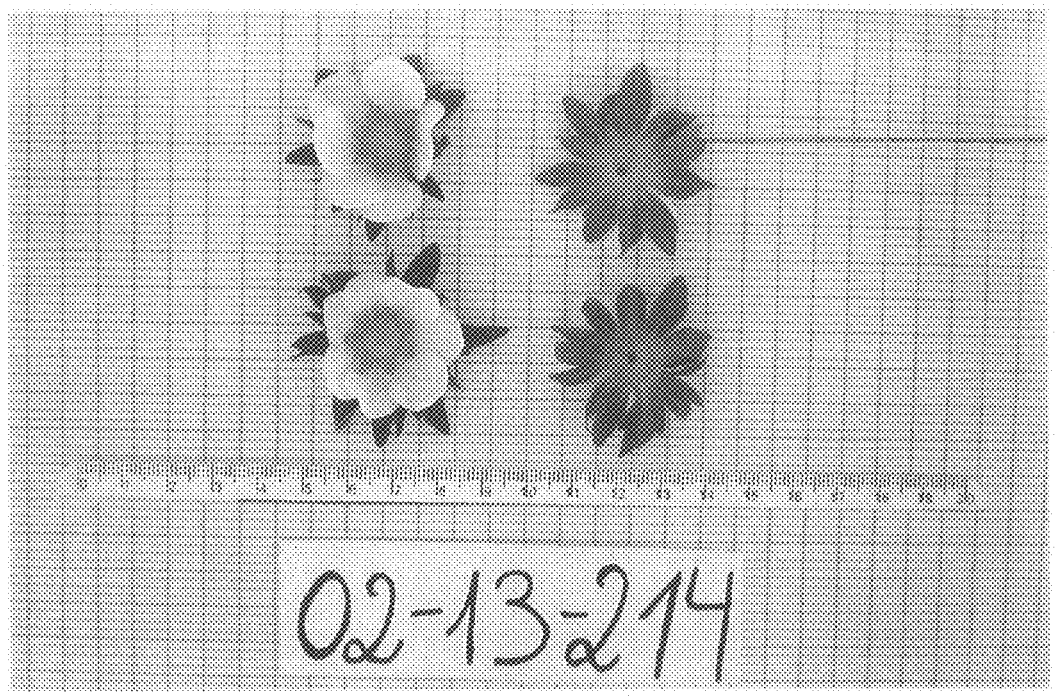

FIG. 8 shows the flower of the new variety (designated 02.13.214). We can see that the size of calyx relative to corolla is bigger.

Figure 9:
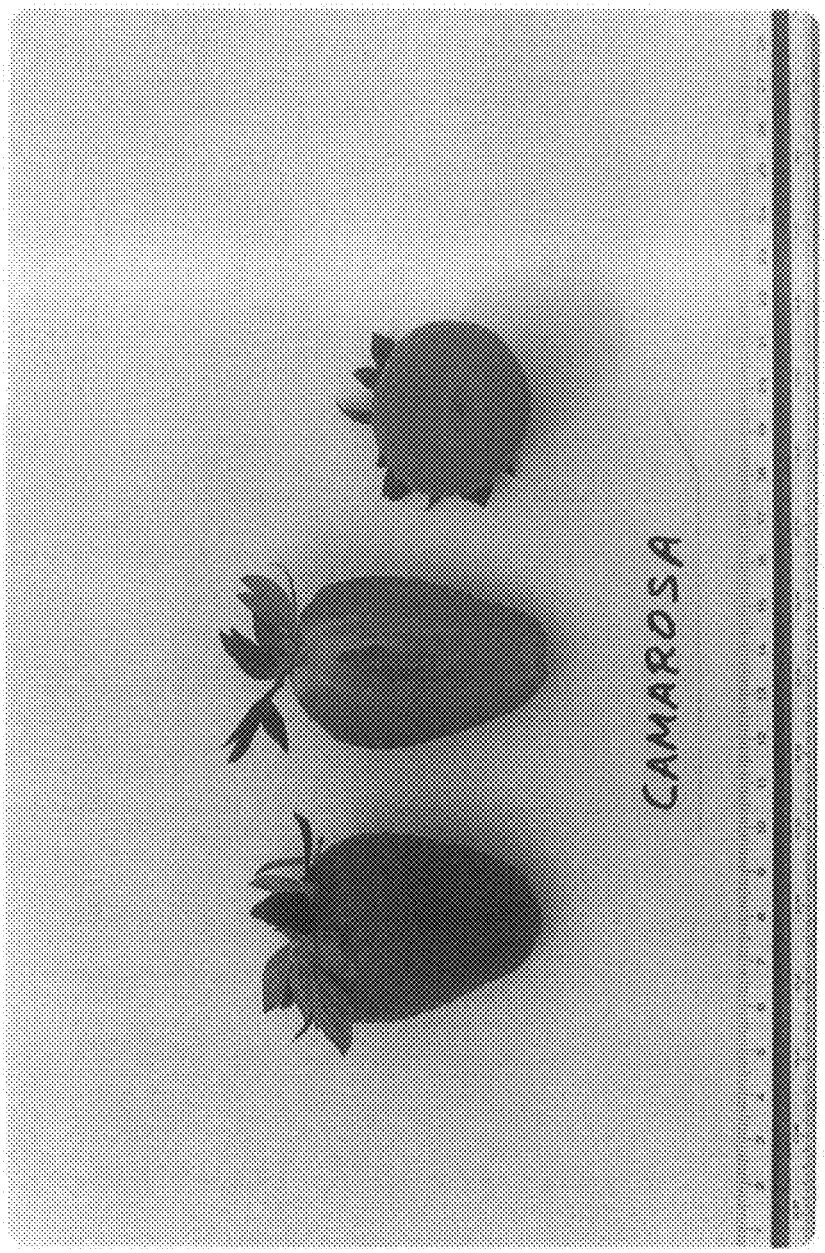

FIG. 9 Shows typical fruits of the strawberry variety 'Camarosa' (U.S. Plant Pat. No. 8,708). In it we can see that the fruit shape of the strawberry variety 'Camarosa' (U.S. Plant Pat. No. 8,708) is wedged and the fruits of the strawberry variety 'Camarosa' (U.S. Plant Pat. No. 8,708) show a dark red fruit color (RHS red group near 47 B to 47A) and a red fruit color of flesh (RHS red group near 42A).

Figure 10:
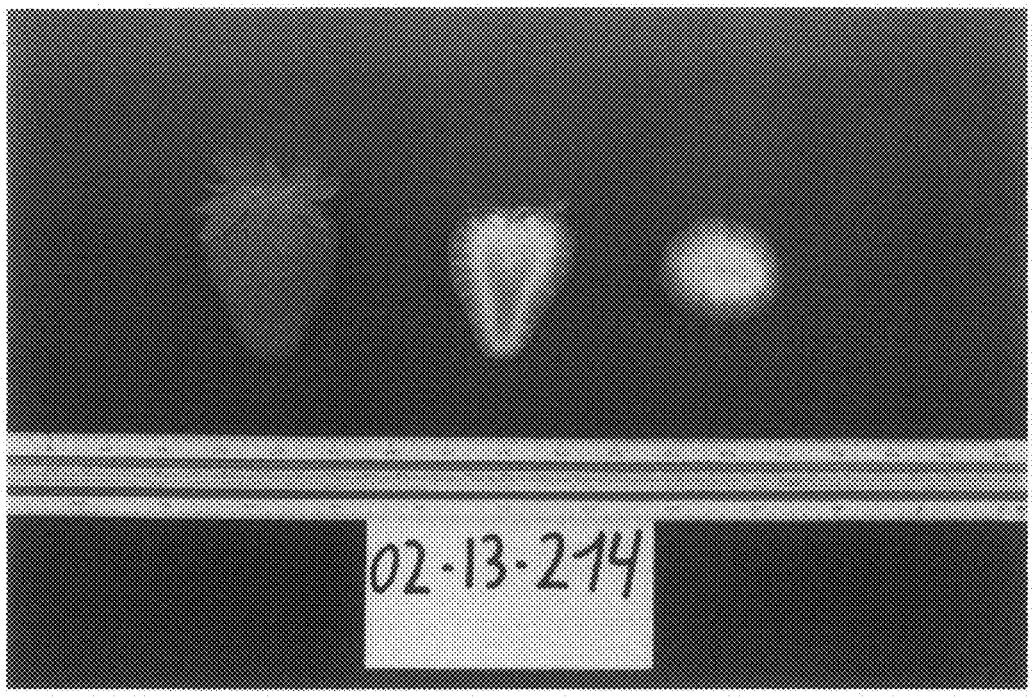

FIG. 10 shows typical fruit of the new variety (designated 02.13.214) whole, sliced and in cross section, illustrating the typical flesh coloration (RHS orange-red group near 33 B to 33 A), with an weakly expressed hollow center, conical shape and red fruit color (RHS red group near 44 B to 44 A).

Figure 11:
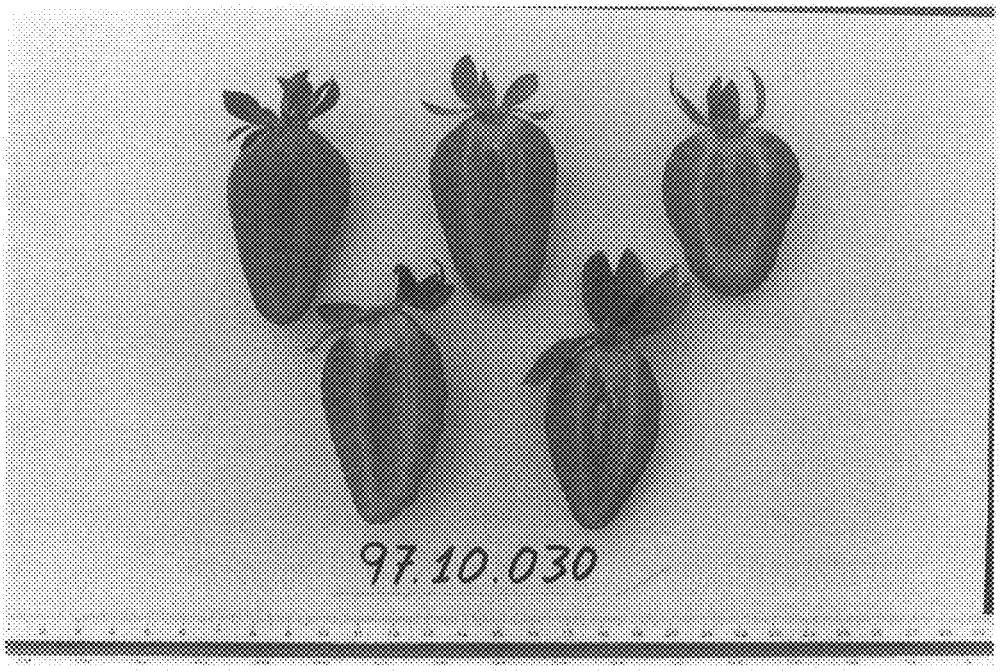

FIG. 11 shows typical fruits of the strawberry variety 'Sabrosa' (U.S. Plant Pat. No. 16,558) (designated 97.10.030). In it we can see that the fruits of the strawberry variety 'Sabrosa' (U.S. Plant Pat. No. 16,558) (designated 97.10.030) show a red fruit color of flesh (RHS read group near 43 B).

DESCRIPTION OF THE NEW VARIETY

The following detailed description of the new variety is based upon observations taken of 2 year old plants and fruits grown "underglass", i.e. undertunnel, in the farm of La Mogalla in Cartaya (Huelva), Spain, 7° W., 37° N., 45 feet elevation.

The following description is in accordance with UPOV terminology and the color terminology herein is in accordance with The Royal Horticultural Society Colour Chart (R.H.S.C.C.), 3rd edition published in 1995. The color descriptions and other phenotypical descriptions may deviate from the stated values and descriptions depending upon variation in environmental, seasonal, climatic and cultural conditions.

PROPAGATION

The new variety is principally propagated by way of runners. Although propagation by runners is presently preferred, other know methods of propagating strawberry plants may be used. Strawberries root well after transplanting.

The term "blistering" used herein refers to the texture or rugosity or surface ondulation inherent to leaves and is generally a constant characteristic.

GENERAL

'PLANASA 02-32' is a short day variety that needs an induction to flowering by chilling, such as occurs at a high elevation nursery (fresh plant) or with cold storage (referred to as a frigo). Usually a short time is sufficient. 'PLANASA 02-32' is self-fertile. It produces large quantity of pollen throughout the seasons and pollination is generally good as there are very few malformed fruit.

Production: Plants described are from high elevation nursery.

Trials pursued in Cartaya (Huelva), Spain.

Date of planting (two years): 10 Oct. 2009 and 11 Oct. 2010.

Number of repetitions (every year): 2.

Plants per repetition (every year): 225.

TABLE ONE

| Accumulated production of 1st quality fruit (g./plant) | | | | |
|---|---|---|---|---|
| Variety | 21-February | 28-March | 25-April | 15-May |
| PLANASA 02-32 | 93 | 445 | 730 | 881 |
| SABROSA | 74 | 405 | 674 | 801 |
| CAMAROSA | 127 | 467 | 747 | 879 |

TABLE 2

| Total yield to 15 May and Fruit Weight average | | | |
|---|---|---|---|
| Variety | 1st + 2nd Quality Fruit | Total | Weight (g/fruit) |
| PLANASA 02-32 | 881 + 95 | 976 | 26-24 |
| SABROSA | 801 + 69 | 870 | 23-22 |
| CAMAROSA | 879 + 146 | 1024 | 24-23 |

TABLE 3

| Production total, to 15 May, of First Quality Fruit ($1^{st}$ quality) and Second Quality Fruit ($2^{nd}$ quality) in g/plant | | | | |
|---|---|---|---|---|
| | TOTAL | | | |
| Variety | $1^{st}$ quality | $2^{nd}$ quality | ($1^{st}$ quality + $2^{nd}$ quality) | % $2^{nd}$ quality |
| PLANASA 02-32 | 881 | 95 | 976 | 9.7 |
| SABROSA | 801 | 69 | 870 | 7.9 |
| CAMAROSA | 879 | 146 | 1024 | 14.3 |

$$\% \ 2^{nd} \text{ quality} = \frac{2^{nd} \text{ quality}}{\text{TOTAL}} \times 100$$

TABLE 4

| Weight (g/Fruit) at two dates: 28 March and 15 May | | |
|---|---|---|
| WEIGHT (g/fruit) | 28 March | 15 May |
| PLANASA 02-32 | 26 | 24 |
| SABROSA | 23 | 22 |
| CAMAROSA | 24 | 23 |

WEIGHT is shown as the average weight per fruit in First Quality Fruits.

TABLE 5

| FRUIT ANALYSIS | | | |
|---|---|---|---|
| | SABROSA | PLANASA 02-32 (02.13.214) | CAMAROSA |
| Firmness (Kg) | 1.30 | 1.35 | 1.20 |
| Soluble Solids (°Brix) | 7.55 | 6.44 | 7.03 |

Firmness: It is the fruit's resistance to penetration measured in Kilograms (Kg). The measure given has been obtained by the penetrometer ROZE Mod. Arbelette, with a 50 $mm^2$ section head.

The following additional information is provided to further describe the new variety.

Variety: 'PLANASA 02-32'. Breeder Ref 02.13.214.

Classification: *Fragaria×ananassa* Duch.

Plant:

*Habit*.—Flat globose.

*Density*.—Medium.

*Vigor*.—Strong.

*Height*.—About 19 cm.

*Width*.—About 22 cm.

Leaf:

*Upperside*.—RHS green group color (near 135 B to 136 B); underside — RHS green group color (near 137 C to 137 B).

*Length*.—About 9.5 cm.

*Width*.—About 14.5 cm.

*Cross section*.—Strongly concave to slightly concave

*Leaf surface ondulation or blistering*.—Medium. The upper side of leaf shows a texture with ondulations neither weak nor strong. The lower side of the leaf shows the veins medium expressed.

*Number of leaflets*.—Three only.

Leaf stem characteristics:

*Color*.—RHS green group (near 141 D to 141 C).

*Position of hairs*.—Strongly outwards.

*Length*.—About 17 cm.

Terminal leaflet:

*Length/width ratio*.—Longer than broad.

*Length*.—About 6.5 cm.

*Width*.—About 7.5 cm.

*Shape of base*.—Acute.

*Shape of teeth*.—Crenate.

Petiole:

*Position of hairs*.—Strongly outwards. The surface of petiole shows a soft texture with few hairs strongly outward.

*Color*.—RHS green group (near 141 D to 141 C).

*Length*.—About 17 cm.

Stipule:

*Anthocyanin coloration*.—Absent or very weak. Length — About 2.5 cm. Color — RHS green group coloration (near 138C to 139 D).

Stolons:

*Number*.—Medium, about 7.

*Thickness*.—Medium, about 3.5 mm.

*Pubescence*.—Medium.

*Color*.—RHS green group (near 141 D to 141 C).

*Length*.—About 22 cm.

Inflorescence:

*Position relative to foliage*.—Level with.

Flower:

*Size*.—Large.

*Size of calyx relative to corolla*.—Larger.

*Spacing of petals*.—Overlapping.

Flower characteristics:

*Diameter primary flowers*.—About 3.0-3.5 cm.

*Diameter secondary flowers*.—About 2.5-3.0 cm.

*Number of petals*.—Normally about 6 to 7. No significant fragrance.

*Time from bloom to mature fruit* (*in Huelva, Spain*).—About 35 to 40 days.

*Stamens*.—About 22-25, with pollen present, fertile and abundant. Length — approximately 4 mm. Color — RHS white group to green-white group (near 157 D to 157 C).

*Anthers*.—Generally average in size. Color — RHS yellow group (near 12 B to 13 B) and darkening with advanced maturity.

*Pollen*.—Fertile and abundant. Color — RHS yellow orange group (near 15 C to 15 B).

*Pistils*.—About 170-210. Color — RHS yellow group (near 12B to 13 B).

Petal:

*Length/width ratio*.—As long as broad.

*Length*.—Approximately 14 to 15 mm.

*Width*.—Approximately 14 to 15 mm.

*Shape*.—Rounded.

*Color*.—RHS white group (near 155 D to 155 C).

Fruiting truss:

*Attitude*.—Semi-erect.

Fruit:

*Ratio of length/maximum width*.—Slightly broader than long.

*Color*.—RHS red group (near 44 B to 44 A).

*Peduncle length of inflorescence stem*.—Primary fruit about 16 to 17 cm, secondary fruit about 11 to 13 cm, color RHS green group (near 141 D to 141 C).

Primary fruit:

*Length*.—About 5.5-6.0 cm.

*Width*.—About 4.0-4.5 cm.

Secondary fruit:

*Length*.—About 5.0-5.5 cm.

*Width*.—About 3.5-4.0 cm.

*Size*.—Large.

*Predominant shape*.—Conical.

*Difference in shapes between primary and secondary fruits*.—Slight.

*Band without achenes*.—Absent or very narrow.

*Color of achenes*.—RHS orange red group (near 33 C to 33 B).

*Unevenness of surface*.—Absent or very weak.

*Evenness of color*.—Even.

*Glossiness*.—Strong.

*Insertion of achenes*.—Below surface.

*Insertion of calyx*.—With fruit level.

*Pose of the calyx segments*.—Reflexed.

*Size of calyx in relation to fruit diameter*.—Slightly larger. The calyx presents 11 to 12 sepals with lanceolate shape.

*Color upperside of sepals*.—Green group (near 135 B to 135 A). Color underside of sepals — Green group (near 138 A to 139 B).

*Length of sepals*.—About 17 to 19 mm.

*Width of sepals*.—About 7 to 8 mm.

*Adherence of calyx*.—Strong.

*Firmness*.—Very firm.

*Color of flesh*.—RHS orange-red group (near 33 B to 33 A).

*Distribution of red color of flesh*.—Only marginal.

*Hollow center*.—Weakly expressed.

*Sweetness*.—Medium. 6,44° Brix.

*Time of flowering* (50% *of plants at first flower*).—Medium.

*Time of ripening* (50% *of plants with ripe fruits*).—Medium.

*Type of bearing*.—Not remontant.

*Chilling*.—Weak.

*Planting date*.—Oct. 11, 2010.

10% *Flowering*.—Dec. 16, 2010.

*First mature fruits*.—Jan. 23, 2011.

*Maturity* (15-20 *gms/plant*).—Feb. 5, 2011.

Time of flowering data: Date of planting: Oct. 11, 2010 in the farm of La Mogalla, in Cartaya (Huelva), Spain, about 7° W, 37° N, 45 feet elevation. 10% flowering occurs about Dec. 16, 2010 with first mature fruit about Jan. 23, 2011 and maturity (15-20 g/plant) about Feb. 5, 2011.

Time of flowers (50% of plants at first flower): About Dec. 24, 2010. Storage Qualities: 'PLANASA 02-32' fruit maintain their quality characteristics when keeping them in a frigo chamber at temperatures of about 2° C. during 48 hours. The fruit's color remains substantially the same.

Time of ripening: After planting as aforesaid, plants are grown in raised beds undertunnel (small tunnel with small holes in plastic walls). Water and fertilizer were applied through drip irrigation. Time of ripening (50% of plants with ripe fruit) is about Jan. 26, 2011. First mature fruit is about Jan. 23, 2011 and maturity (15-20 gms/plant) is about Feb. 5, 2011.

General: The growing period in Huelva, Spain, where the observations were made, is between about December,10 and May,15 of each year, with a maximum production at about beginning-April. 'PLANASA 02-32' is a short variety that benefits from induction to flowering by chilling, usually a few hours are sufficient, preferably at temperatures of 7° C. or less. Normally, the minimum number of hours is accumulated in the field during several days.

Disease resistance: No particular sensitivity to any disease or parasite has been observed for 'PLANASA 02-32'.

I claim:

1. A new and distinct strawberry plant of the variety substantially as shown and described.

* * * * *

UNITED STATES PATENT AND TRADEMARK OFFICE

CERTIFICATE OF CORRECTION

PATENT NO. : PP23,903 P3
APPLICATION NO. : 13/317795
DATED : September 17, 2013
INVENTOR(S) : Alexandre Pierron-Darbonne It is certified that error appears in the above-identified patent and that said Letters Patent is hereby corrected as shown below:

On the Title Page, Specification

Col. 1, line 1 — Delete "Pragaria×ananassa",
Insert -- Fragaria × ananassa --

Signed and Sealed this
Third Day of February, 2015

Michelle K. Lee

Michelle K. Lee
*Deputy Director of the United States Patent and Trademark Office*